US008591489B2

(12) United States Patent
Van Bogart

(10) Patent No.: US 8,591,489 B2
(45) Date of Patent: Nov. 26, 2013

(54) REUSABLE DIAPER

(76) Inventor: Sarah B. Van Bogart, Andover, MN (US)

( * ) Notice: Subject to any disclaimer, the term of this patent is extended or adjusted under 35 U.S.C. 154(b) by 1062 days.

(21) Appl. No.: 12/571,000

(22) Filed: Sep. 30, 2009

(65) Prior Publication Data
US 2011/0077611 A1 Mar. 31, 2011

(51) Int. Cl.
A61F 13/15 (2006.01)

(52) U.S. Cl.
USPC .................... 604/385.15; 604/392

(58) Field of Classification Search
USPC .......... 604/385.15, 392–395; 2/400–408, 238
See application file for complete search history.

(56) References Cited

U.S. PATENT DOCUMENTS

| 3,916,901 | A | * | 11/1975 | Korgemets ................ 604/392 |
| 4,883,481 | A | * | 11/1989 | Blanchard ............... 604/385.11 |
| 5,032,119 | A | | 7/1991 | Hookano |
| 5,069,672 | A | | 12/1991 | Wippler et al. |
| 5,137,526 | A | | 8/1992 | Coates |
| 5,181,915 | A | | 1/1993 | Smith |
| 5,209,743 | A | | 5/1993 | Hardison |
| 5,261,901 | A | | 11/1993 | Guay |
| 5,342,340 | A | | 8/1994 | Kichefski et al. |
| 5,356,402 | A | | 10/1994 | Gillies et al. |
| 5,368,585 | A | | 11/1994 | Dokken |
| 5,409,476 | A | | 4/1995 | Coates |
| 5,725,518 | A | | 3/1998 | Coates |
| 5,784,723 | A | * | 7/1998 | Noble et al. ................ 2/400 |
| 6,579,273 | B2 | | 6/2003 | Dupuy |
| 6,623,467 | B1 | | 9/2003 | Charles-Lundaahl |
| 7,575,573 | B1 | | 8/2009 | Roe et al. |
| 7,914,507 | B1 | | 3/2011 | Magee |
| 2002/0095132 | A1 | | 7/2002 | Ashton et al. |
| 2008/0183148 | A1 | | 7/2008 | Labit et al. |
| 2008/0195075 | A1 | | 8/2008 | Ruocco |
| 2008/0215027 | A1 | | 9/2008 | Labit et al. |
| 2009/0187156 | A1 | | 7/2009 | Anzalone |
| 2009/0240228 | A1 | | 9/2009 | Nonnenmann et al. |
| 2012/0041408 | A1 | | 2/2012 | Van Bogart |

OTHER PUBLICATIONS

European Search Report for related EP Application No. 10820930.5, dated Feb. 28, 2013; 6 pgs.
Office Action dated Jun. 5, 2012 for related U.S. Appl. No. 13/282,173, 16 pgs.
International Search Report and Written Opinion from related PCT Application No. PCT/US2010/002376, dated May 26, 2011, 9 pgs.
International Preliminary Report on Patentability from related PCT Application No. PCT/US2010/002376, dated Apr. 12, 2012, 6 pgs.

* cited by examiner

Primary Examiner — Jackie Ho
Assistant Examiner — Peter S Vasat
(74) Attorney, Agent, or Firm — Brooks, Cameron & Huebsch, PLLC

(57) ABSTRACT

The present disclosure provides reusable diaper devices, systems, and methods. One diaper embodiment includes a diaper body layer, a first casing formed from one or more layers of material and positioned on the diaper body layer, a first channel is formed by the casing proximate to a first leg opening of the diaper and the first channel contains a first band, a second casing formed from one or more layers of material and positioned on the diaper body layer, a second channel is formed in the casing proximate to a second leg opening of the diaper and the second channel contains a second band, and a length of each of the bands is adjustable.

20 Claims, 6 Drawing Sheets

007# REUSABLE DIAPER

BACKGROUND

Diapers have been used to contain the waste of infants, toddlers, and in some cases, other individuals who do not have control of their bladders and bowel movements. Diapers can be made of a reusable fiber, such as cotton, and/or they can be made of disposable materials, such as a plastic and cotton combination.

In some designs, reusable diapers have been made of a single piece of cotton fabric and were fastened around a wearer's waist and legs. Safety pins have been used to fasten the ends of the single piece of cotton fabric together.

It can be difficult for single piece cotton fabric reusable diapers to achieve a proper fit on a wearer's leg due to many factors, such as the size of the diaper, size of the wearer, shape or the diaper, shape of the wearer, the number of fastening mechanisms used, and other factors. If the diaper is pulled too tight it can be uncomfortable for the wearer and if the diaper is too loose leakage can occur around the legs of the wearer.

Disposable diapers can be made of a combination of plastics and soft fiber materials, such as cotton. The plastic can, for example, provide waterproof characteristics to prevent leakage through the soft fiber material portion. The soft fiber material portion can provide absorption for the waste of the wearer.

Disposable diapers have been readily available in most developed countries and can be desirable because the diaper can be disposed of in the trash without having to handle or dispose of the waste in the diaper separately. However, disposable diapers can be undesirable, for example, because the chemicals used to make the diapers can be harmful to the wearers. Also, disposable diapers can create strain on the environment because a diaper is disposed of in the trash each time a wearer creates waste while wearing a disposable diaper and these types of diapers are not typically readily degradable.

In contrast, reusable diapers can be desirable because of the reduced harmful environmental impact over disposable diapers, the ability to choose chemical-free materials, and the reduced overall cost due the fixed cost of buying fewer diapers and reusing them.

DETAILED DESCRIPTION

Figure 1:
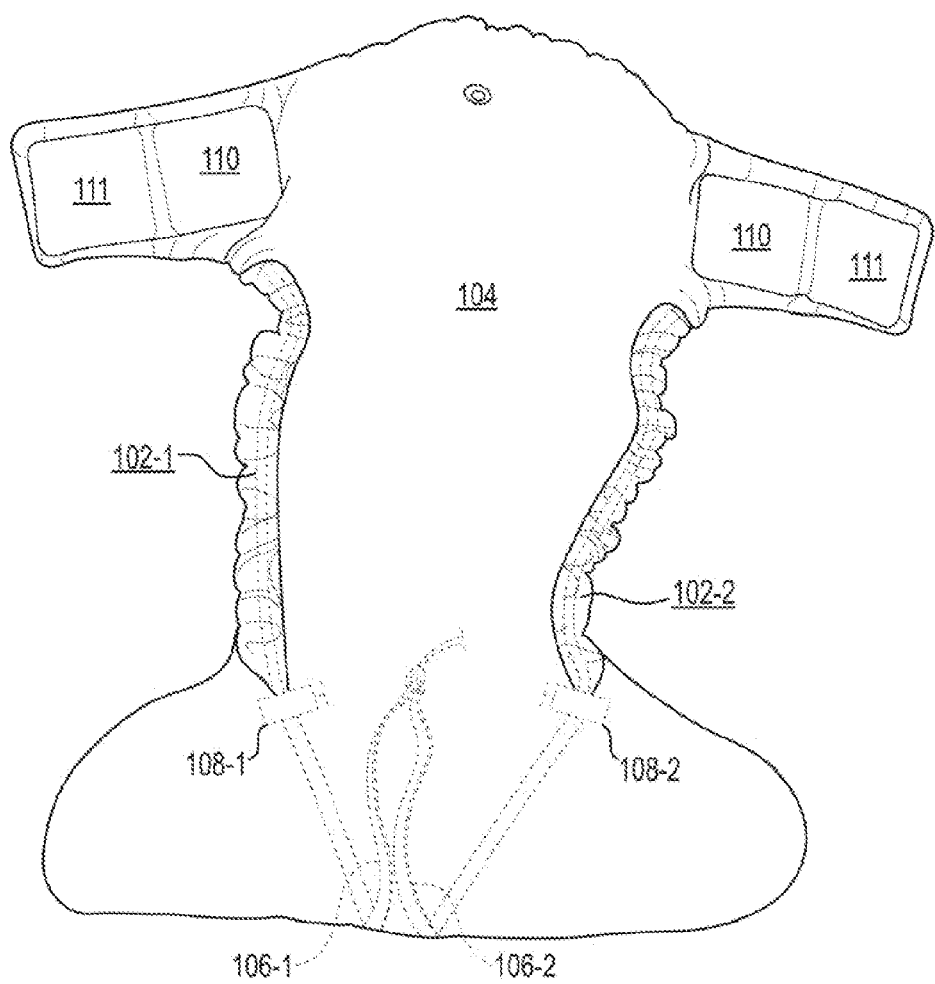
FIG. 1 illustrates a reusable diaper viewed showing the inner layer according to an embodiment of the present disclosure.

The present disclosure provides reusable diaper devices, systems, and methods. For example, in various embodiments, a reusable diaper can include a diaper body layer with a first casing formed from one or more layers of material and a first channel formed in the casing proximate to a first leg opening of the diaper. A second casing can be formed from one or more layers of material and a second channel can be formed in the casing proximate to a second leg opening of the diaper.

The first channel can contain a first band and the second channel can contain a second band. The first band can be fixed to one or more of the diaper body layer and the first casing at a first end of the first channel and the second band can be fixed to one or more of the diaper body layer and the second casing at a first end of the second channel. A length of each of the bands in the channels can be adjusted at the second end of each of the channels.

In one or more embodiments, the length of the band in each channel can be adjusted at any point along at least a portion of its length. In some embodiments, adjustable stop mechanisms can be provided on the bands. The adjustable stop mechanisms and the bands can be accessible in an opening. The opening can be in the diaper body layer and/or between one or more layers of material, among other locations on the reusable diaper.

In one or more embodiments, the first and second casings can be formed by the diaper body layer. In some embodiments, the first casing can be coupled proximate to a first leg opening portion of the diaper body layer and the second casing can be coupled proximate to a second leg opening portion of the diaper body layer. And, in some embodiments, at least one of the first channel and the second channel narrows at the second end of the channel to prevent the corresponding adjustable stop mechanism from entering its respective channel.

The length of the channel can, for example, be sized in correlation to the size of the diaper. The elastic should be longer than the channel when the channel is straight so that it can be accessed by a user in order to adjust its length as discussed in more detail below.

In some embodiments, the adjustment can be through use of stop mechanisms. In some such embodiments, the first channel and the second channel can narrow at the second end of the channels to prevent the stop mechanism from entering one or both of the channels.

Various embodiments can include a method of forming a reusable diaper by forming a first channel positioned between an inner layer and an outer layer proximate to a first leg opening portion of a diaper and forming a second channel between the inner layer and the outer layer proximate to a second leg opening portion of the diaper. Methods can also include fixing a portion of a first band proximate to a first end of the first channel and placing the band in an adjustable stop mechanism that holds the band in place at any number of locations on the band at a second end of the first channel. Also, method embodiments can include fixing a portion of a second band proximate to a first end of the second channel and placing the band in an adjustable stop mechanism that holds the band in place at any number of locations on the band at a second end of the second channel.

In one or more embodiments, the bands can be adjusted at the second ends of the channels to fit a wearer's leg. In various embodiments, an absorption layer can be inserted between the inner layer and the outer layer.

In some embodiments, an absorption layer can be inserted adjacent to an outer surface of the inner layer wherein the absorption layer is positioned to be between the inner layer and a wearer. The method of forming a reusable diaper can include placing the diaper around the waist and legs of a wearer by coupling a first end of the diaper to a second end of the diaper.

In various embodiments, a reusable diaper system can include a diaper body having an outer layer and an inner layer, wherein the outer layer can include a fastening mechanism that couples a first end of the outer layer to a second end of the outer layer to form a first opening and a second opening for a wearer's leg to be placed through. A first channel can be formed between the outer layer and the inner layer and proximate to a first leg opening portion of the diaper and wherein the first channel contains a first band.

A second channel can be formed between the outer layer and the inner layer and proximate to a second leg opening portion of the diaper and wherein the second channel contains a second band. In some embodiments, the first band can be fixed to the diaper body at a first end of the first channel, the second band can be fixed to the diaper body at a first end of the second channel, and a length of each of the bands in the channels can be adjusted at a second end of each of the channels.

In one or more embodiments, an absorption layer can be positioned between the outer layer and the inner layer and the inner layer can include an opening to receive the absorption layer between the outer layer and the inner layer. In some embodiments, an absorption layer can be adjacent to an outer surface of the inner layer and wherein the absorption layer is positioned to be between the inner layer and a wearer. In various embodiments, the fastening mechanism that couples the first end of the outer layer to the second end of the outer layer are selected from the group consisting of a button, a snap, a pin, and hook and loop fasteners.

In one or more embodiments, a first adjustable stop mechanism can be provided on the first band and a second adjustable stop mechanism can be provided on the second band. The first and second adjustable stop mechanisms and their respective channels can be constructed and arranged to prevent the first and second adjustable stop mechanisms from entering the second end of their respective channel and the first and second adjustment stop mechanisms prevent the portion of the bands outside of each respective channel from entering the channel. In some embodiments, the first and second adjustable stop mechanisms can be accessible via an opening in the diaper body.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure.

The Figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2.

As will be appreciated, elements shown in the various embodiments herein can be added, exchanged, and/or eliminated so as to provide a number of embodiments of the present disclosure. In addition, the proportion and the relative scale of the elements provided in the figures are intended to illustrate various embodiments of the present invention and are not to be used in a limiting sense.

FIG. 1 illustrates a reusable diaper viewed showing the inner layer according to an embodiment of the present disclosure. The inner layer is typically made from a soft material as the layer may be in contact with the wearer. For example, the inner layer 104 of the reusable diaper can be made of fleece material, however, any other suitable material may be used in various embodiments. In some embodiments, the inner layer 104 can be coupled to an outer layer illustrated as 212 in FIG. 2 along its perimeter by a coupling mechanism, such as thread.

In FIG. 1, the diaper can include a first channel 102-1 and a second channel 102-2. The first channel 102-1 and the second channel 102-1 can be defined by a casing for each channel. As used herein, a casing is an elongated tube that forms a channel therein. The channel allows a portion of a band of material (i.e., any elastic of inelastic elongate material suitable for the purposes described herein) to be slidably received therein which provides for adjustability of the leg opening portion of the diaper.

The casing can be formed by one or more layers of material or materials. For example, the casings defining the first channel 102-1 and/or the second channel 102-1 can be material used to form the inner layer, material used to form a layer attached to the inner layer (e.g., outer layer), or other material that is attached to the inner layer to firm one or more of the casings. Although the layer 104 shown is described as the inner layer with respect to FIG. 1, it should be understood that in some embodiments, there may be only one layer and it may be similar to the inner layer described in FIG. 1.

In various embodiments, the casing is positioned on a portion of the inner layer 104 defined by an area proximate to the leg opening portion of the diaper. For example, the casing may be provided between a leg opening portion of the diaper used to form a leg opening and a line approximately 0.5 inches from the leg opening portion and located between the flared ends of the diaper.

A first band 106-1 can be included in first channel 102-1 and a second band 106-2 can be included in second channel 102-2. The first elastic band 106-1 and the second band can be fixed at a first end of first channel 102-1 and a first end of second channel 102-2, respectively.

In some embodiments, the second end of first channel 102-1 and the second end of second channel 102-2 can narrow, forming an opening at the second end of the channels. This can be beneficial in keeping a stop mechanism from entering the channel, in some embodiments. As illustrated in FIG. 1, in some embodiments, the bands 106-1 and 106-2 can exit the channels at the opening of the second end of their respective channels.

In various embodiments, as illustrated in FIG. 1, the bands 106-1 and 106-2 can include adjustable stop mechanisms 108-1 and 108-2, respectively. Adjustable stop mechanisms 108-1 and 108-2 can be outside of channels 102-1 and 102-2. In some such embodiments, the stop mechanisms can be prevented from entering channels 102-1 and 102-2 by being larger than the opening at the ends of channels 102-1 and 102-2.

In the embodiment illustrated in FIG. 1, the bands 106-1 and 106-2 are placed through openings in the stop mechanisms 108-1 and 108-2. The openings in the stop mechanism can at least partially close and be held in place on the bands 106-1 and 106-2 under force exerted by springs in the stop mechanisms 108-1 and 108-2. Such stop mechanisms can be moved along the bands to control the length of band that is in the channel. The length of the bands that is in the channels can vary with size of the wearer's leg opening and the tension that the elastic puts on a wearer's leg when the diaper is placed upon a wearer. Therefore, the opening for the wearer's leg can vary in size and in tension around the wearer's leg allowing the diaper to be used on various sized legs.

In some embodiments, as illustrated in FIG. 1, the inner layer can include a number of fastener portions (e.g., 110 and/or 111, in FIG. 1) that can be used to couple one end of the diaper to a second end of the diaper forming openings that can surround a wearer's legs thereby improving the fit of the diaper around the legs of the wearer. In some embodiments, the adjustability of the legs in combination with the adjustability of the fastener portions can provide the wearer with a significantly improved fit.

The fastening mechanisms can be any suitable mechanism. For example, in some embodiments, a fastening mechanism can include a button, snap, pin, a hook and look fastener, among other types.

Coupling the ends of the diaper together when placed on a wearer can create on opening in the diaper that is around the waist of the wearer and two openings that are around the legs of a wearer. In embodiments of the present disclosure, the openings for the legs include casings that define the channels containing the bands.

The bands in the channels proximate the leg opening portions of the diaper can create tension around the legs of the wearer. This tension provides a seal around the legs of a wearer to prevent waste from leaking through the leg opening of the diaper. The adjustment mechanism can be used to vary the length of band that is in the channel and therefore vary size of the leg opening. This size change then varies the tension that the leg opening exerts on the wearer's legs (i.e., a smaller leg opening with increase the tension on the leg of the wearer as the diaper will fit tighter around the wearer's legs.

In some embodiments, when the leg openings are stretched by a wearer, the adjustable stop mechanisms are pulled to the end of the channels, where they are prevented from entering the channels. In such embodiments, the fixed end of the bands and the adjustable stop mechanisms limit the degrees of freedom for movement of the bands in the channels thus creating the tension and elastic expansion and contraction of the bands in the channels.

Some embodiments of the present disclosure can be a single layer of material, wherein the casings are positioned on the inside or outside of the layer. In some embodiments, multiple layers can be utilized as discussed below with respect to one such embodiment illustrated in FIG. 2, where the diaper body is constructed of 2 layers, an inner layer and an outer layer.

Figure 2:
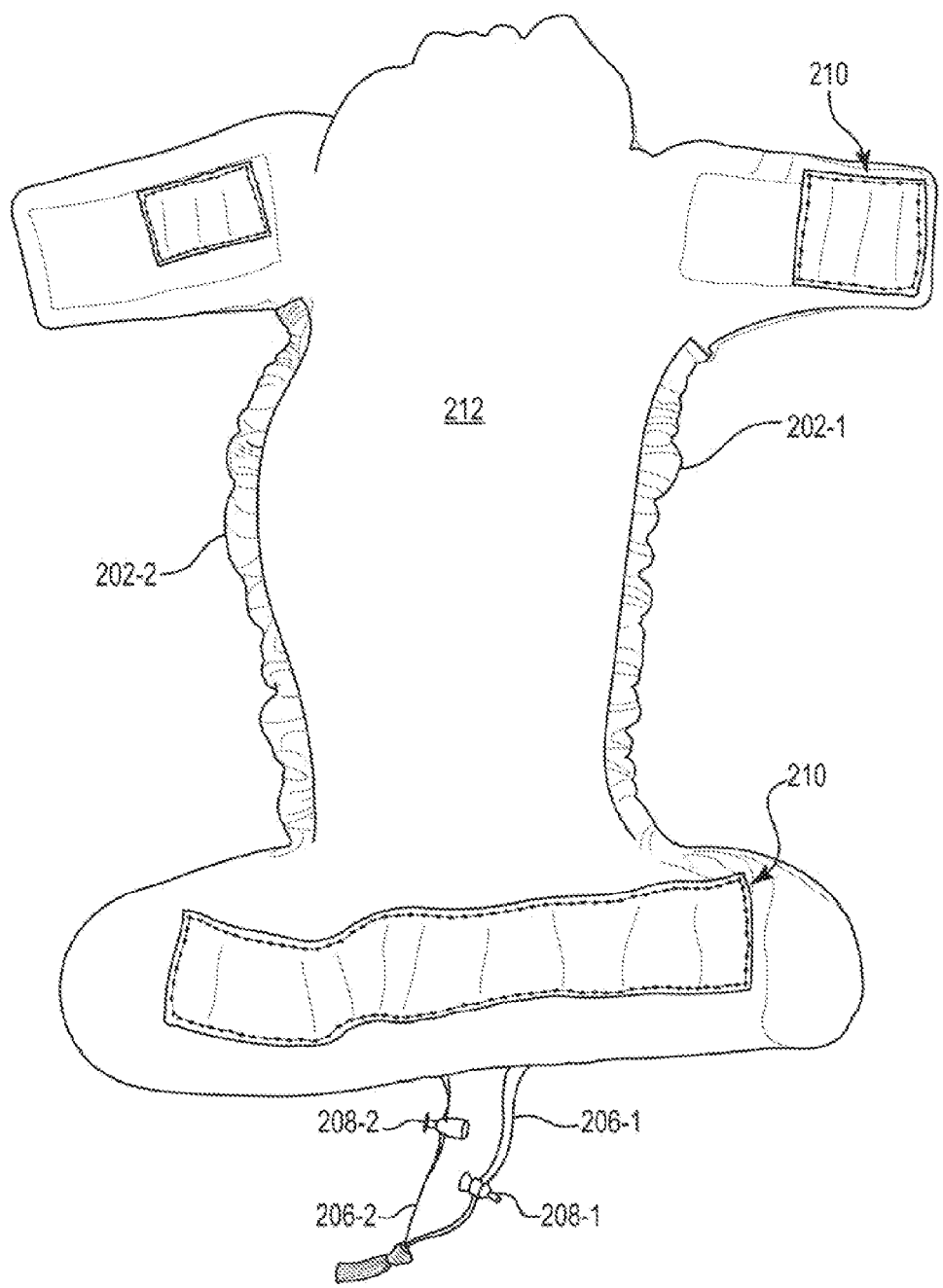
FIG. 2 illustrates an outer layer of a reusable diaper according to an embodiment of the present disclosure.

FIG. 2 illustrates an outer layer of a reusable diaper according to an embodiment of the present disclosure. The use of multiple layers can be done for a variety of reasons (e.g., aesthetics, waterproof or water resistant materials to protect other objects from the waste in side the diaper, different materials to improve the tactile feel of the diaper, etc).

The outer layer 212 can be coupled to an inner layer (not shown) along its perimeter by a coupling mechanism, such as thread, glue, or any other suitable attachment mechanisms. The outer layer 212 can include a number of hook and/or loop fastener portions 210 and 211 that can be used to couple one end of the diaper to a second end of the diaper forming openings that can surround a wearer's legs.

FIG. 2 also illustrates two casings 202-1 and 202-2 proximate to the leg opening portions of the outer layer 212 of the diaper body.

Figure 3:
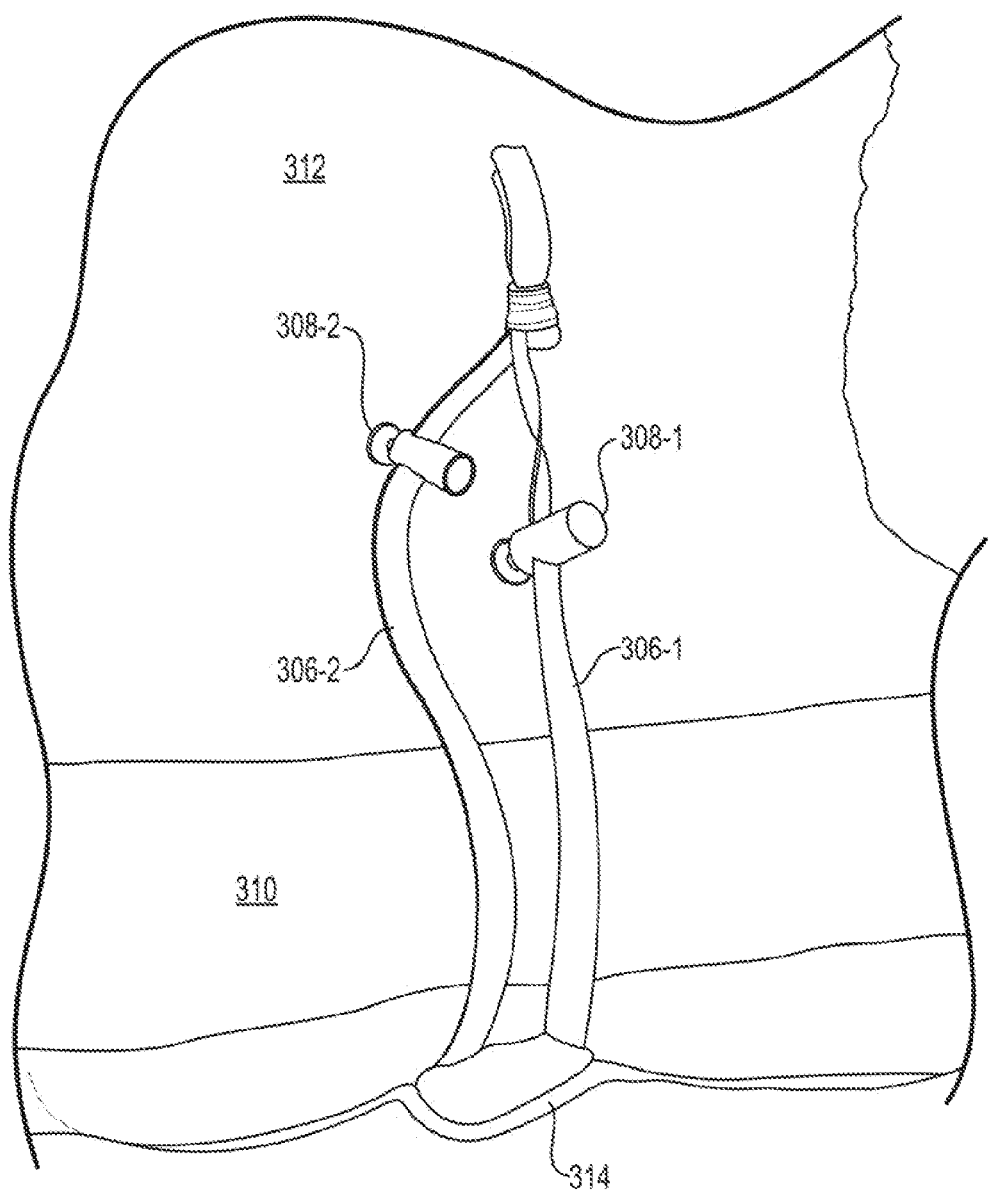
FIG. 3 illustrates bands and adjustable stop mechanisms of a reusable diaper according to an embodiment of the present disclosure.

FIG. 3 illustrates bands and adjustable stop mechanisms of a reusable diaper according to an embodiment of the present disclosure. FIG. 3 illustrates a multiple layer diaper having an inner layer and an outer layer.

In the embodiment illustrated in FIG. 3, opening 314 can be created by a gap in the coupling of the inner layer and the outer layer proximate to (i.e., at or near) their perimeters. Opening 314 can allow access to the bands 306-1 and 306-2 and the stop mechanisms 308-1 and 308-2. In various embodiments, an opening to access the bands and the stop mechanisms can be in one or more locations on a reusable diaper.

In the embodiment illustrated in FIG. 3, when a diaper is in use, the bands 306-1 and 306-2 and the stop mechanisms 308-1 and 308-2 can be placed between the inner layer and the outer layer 312 through opening 314. in some embodiments, when adjusting the length of band in the channel, the bands 306-1 and 306-2 and the stop mechanisms 308-1 and 308-2 can be brought outside of the diaper through opening 314, as illustrated in FIG. 3. In various embodiments, when adjusting the length of band in a channel, the one or more openings can be sized to allow the user to place their hand between the inner and outer layers. In some embodiments, the layers or a portion thereof can be releasable such that the user can pull them apart to adjust the bands and then attach the layers back together.

Also illustrated in FIG. 3 is a fastener portion 310 (e.g., hook and loop fasteners) to allow the other end of the diaper to couple to the end shown in FIG. 3 when placing the diaper on a wearer, as discussed above. In some embodiments, other layers can be provided with the inner and/or outer layers discussed above. For example, an absorption layer can be utilized in some embodiments. An absorption layer can be used in addition to or instead of an absorbent inner layer.

Figure 4:
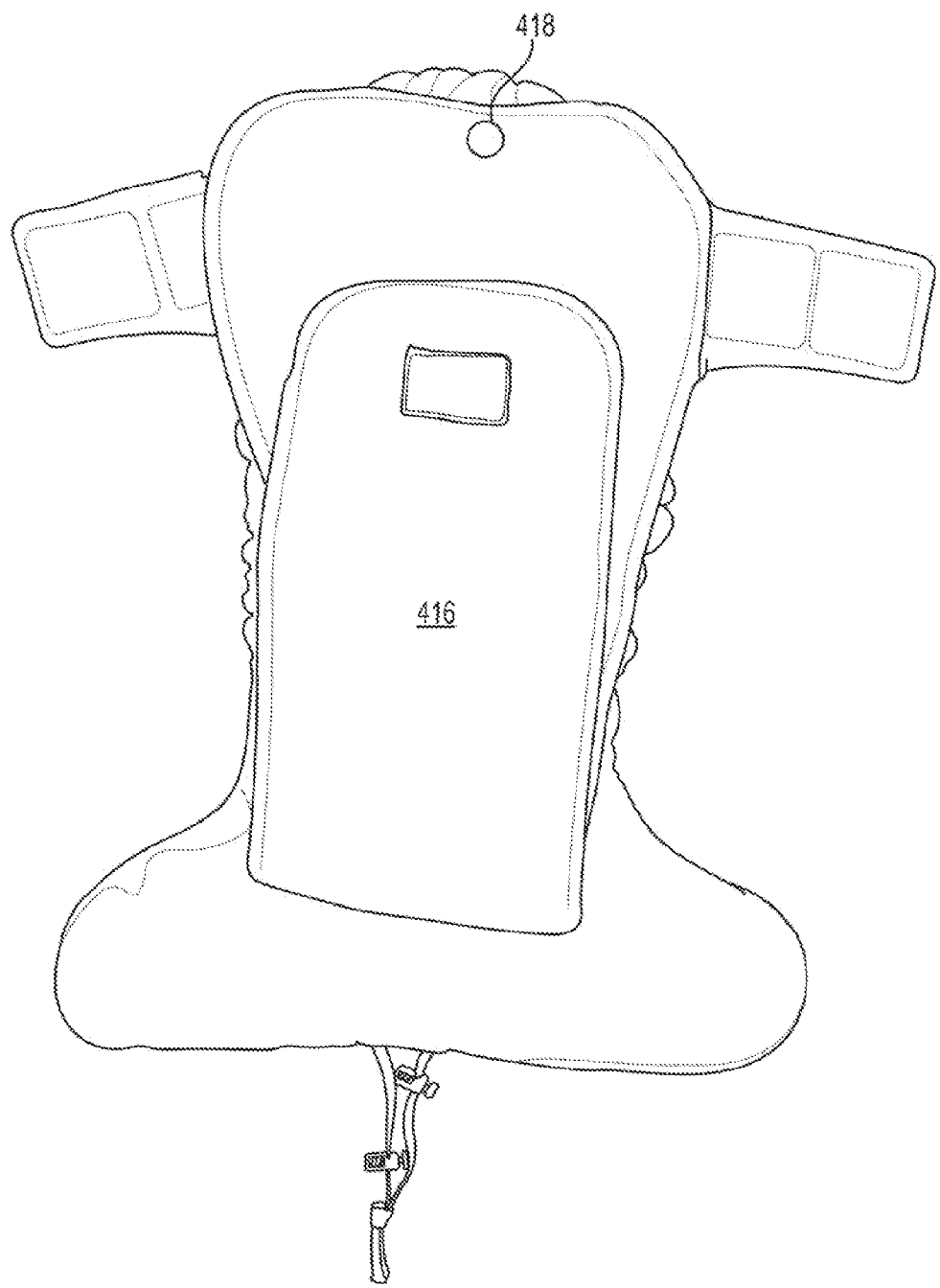
FIG. 4 illustrates an absorption layer of a reusable diaper according to an embodiment of the present disclosure.

FIG. 4 illustrates an absorption layer of a reusable diaper according to an embodiment of the present disclosure. In the embodiment of FIG. 4, an absorption layer 416 is placed on the inner layer. Although described herein as an absorption layer, such a layer can be utilized to retain and/or absorb waste from a wearer of the diaper. The absorption layer can, for example, prevent waste from contacting the inner and/or outer layer of the diaper, thus allowing the absorption layer to be removed and replaced with a clean absorption layer after a diaper is soiled. Therefore, in such implementations, absorption layers may need to be laundered regularly and the diaper body layer does not need to be laundered each time a diaper is soiled.

The absorption layer can be positioned adjacent to the inner layer and/or attached to the inner layer, in various embodiments. In the embodiment of FIG. 4, the absorption layer 416 is coupled to the inner layer. The absorption layer 416 can be coupled to the inner layer with any suitable coupling mechanism. For example, the coupling mechanism can be a snap 418, as illustrated in the embodiment of FIG. 4, among other coupling mechanisms.

Figure 5:
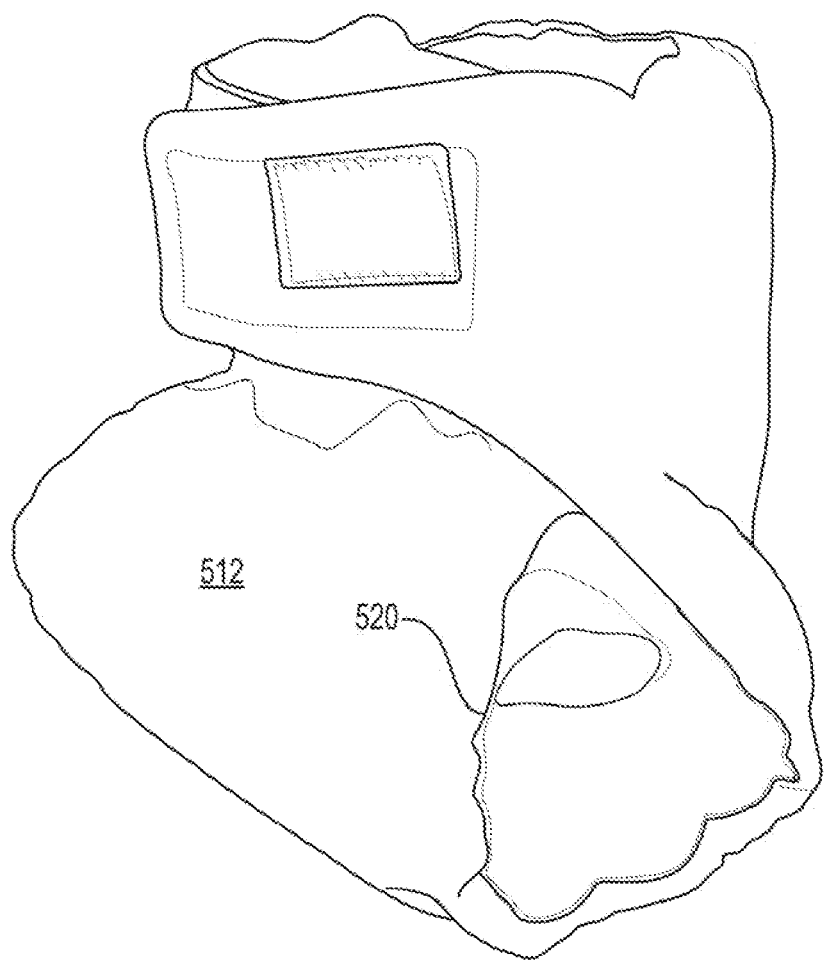
FIG. 5 illustrates a reusable diaper positioned for use according to an embodiment of the present disclosure.

FIG. 5 illustrates a reusable diaper positioned for use according to an embodiment of the present disclosure. In FIG. 5, the diaper is adjusted and coupled together for use on an infant and/or toddler.

When using the diaper, the upper side portions of the diaper are coupled together using a fastening mechanism to fit the diaper on the waist of a wearer. If an adjustable fastening mechanism is used, the fastening mechanism can allow the diaper to be adjustable based on the size of the wearer. Coupling these portions of the diaper together forms openings for the legs of the wearer (e.g., opening 520 of FIG. 5). Opening 520 has a channel proximate to its leg opening portion that contains an band. The length of the band can be adjusted, for example, by using stop mechanisms, therefore the tension provided by the bands at the opening can be adjusted by the stop mechanisms. The tension provided by the bands at the opening can allow the diaper to fit a wearer's legs and prevent waste from leaking from the diaper.

Figure 6:
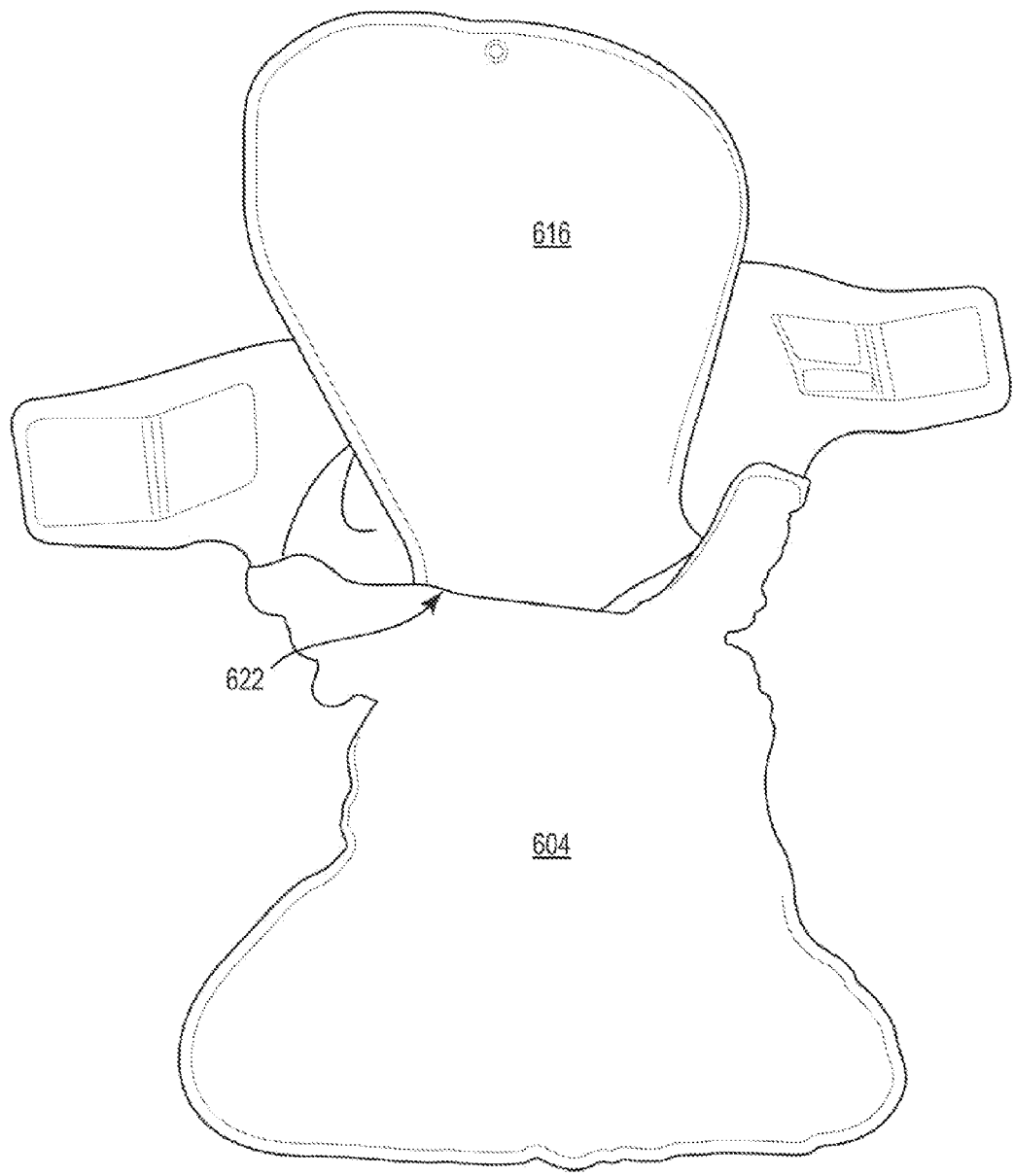
FIG. 6 illustrates an opening of a reusable diaper for an absorption layer according to an embodiment of the present disclosure.

FIG. 6 illustrates an opening of a reusable diaper for an absorption layer according to an embodiment of the present disclosure. In FIG. 6, an absorption layer 616 is placed between the inner layer 604 and the outer layer (not shown) through opening 622. Opening 622 can provide access for adding and removing an absorption layer from the diaper.

In various embodiments, an absorption layer can be placed between the inner and outer layer. In such embodiments, the inner layer and the absorption layer combine to absorb and contain the waste as discussed above with respect to the absorption layer of FIG. 5. In such embodiments, the inner layer and absorption layer can be laundered after the diaper has been soiled. The absorption layer between the inner and outer layer can prevent and/or limit waste from soiling the outer layer, reducing the need to launder the outer layer each time the diaper is soiled.

In one or more embodiments, an absorption layer can be placed between the inner and outer layer along with another absorption layer that can be placed on the inner layer. In this configuration, the absorption layer on the inner layer can absorb the majority of the waste in the diaper, so this absorption layer can be the primary portion of the diaper that needs to be laundered after a diaper is soiled.

The absorption layer between the inner and outer layers can then be used as a back-up to the absorption layer on the inner layer, and to some degree the inner layer, for large amounts of waste that the absorption layer on the inner layer, and the inner layer, cannot absorb on its own. The absorption layer between the inner and outer layers can protect the outer layer from waste, therefore minimizing the need for cleaning the outer layer.

The opening can be positioned a in various locations in the diaper body. In the embodiment of FIG. 6, opening 622 is position in the inner layer 604 and is positioned such that the opening 622 will be positioned on the wearer's back, which can be beneficial as the wearer will not have to sit on the edges of the opening and the opening may be more easily accessible to a user.

The opening may have various suitable types of closure structures. In the embodiment of FIG. 6, the opening 622 is constructed so that the edges of the fabric forming the opening overlap. Such a structure aids in keeping the absorbent layer in between the inner and outer layers. Such a structure also may be more comfortable to a wearer, in some implementations.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

Although specific embodiments have been illustrated and described herein, those of ordinary skill in the art will appreciate that an arrangement calculated to achieve the same techniques can be substituted for the specific embodiments shown. Combination of the above embodiments, and other embodiments not specifically described herein will be apparent to those of skill in the art upon reviewing the above description. The scope of the various embodiments of the invention includes other applications in which the above structures and methods can be used. Therefore, the scope of various embodiments of the invention should be determined with reference to the appended claims, along with the full range of equivalents to which such claims are entitled.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The present disclosure provides reusable diaper devices, systems, and methods. In various embodiments, a reusable diaper can include a diaper body layer with a first casing formed from one or more layers of material and a first channel formed in the casing proximate to a first leg opening of the diaper. A second casing can be formed from one or more layers of material and a second channel can be formed in the casing proximate to a second leg opening of the diaper. The first channel can contain a first band and the second channel can contain a second band. The first band can be fixed to one or more of the diaper body layer and the first casing at a first end of the first channel and the second band can be fixed to one or more of the diaper body layer and the second casing at a first end of the second channel. A length of each of the bands in the channels can be adjusted at the second end of each of the channels.

What is claimed is:

1. A reusable diaper, comprising:
 a diaper body including a first layer adapted to face away from a wearer and a second layer adapted to face toward the wearer;
 a first casing formed from one or more layers of material and positioned on the diaper body;
 wherein a first channel is formed by the casing proximate to a first leg opening of the diaper body and wherein the first channel contains a first band;
 a second casing formed from one or more layers of material and positioned on the diaper body;
 wherein a second channel is formed in the casing proximate to a second leg opening of the diaper body and wherein the second channel contains a second band;
 wherein a first end of the first band is fixed to one or more of the diaper body and the first casing at a first end of the first channel and wherein a first end of the second band is fixed to one or more of the diaper body and the second casing at a first end of the second channel;

wherein a length of the first band in the first channel is adjustable at the second end of the first channel via a first adjustment mechanism at a second end of the first channel and wherein a length of the first band outside of the first channel and the first adjustment mechanism are adapted to be positioned between the first layer and the second layer of the diaper body; and wherein a length of the second band in the second channel is adjustable at the second end the second channel via a second adjustment mechanism at a second end of the second channel and wherein a length of the second band outside of the second channel and the second adjustment mechanism are adapted to be positioned between the first layer and the second layer of the diaper body.

2. The reusable diaper of claim 1, wherein the length of the first band in the first channel is adjustable via the first adjustment mechanism at any point along at least a portion of its length and wherein the length of the second band in the second channel is adjustable via the second adjustment mechanism at any point along at least a portion of its length.

3. The reusable diaper of claim 1, wherein the first adjustable stop mechanism is provided on the first band and the second adjustable stop mechanism is provided on the second band.

4. The reusable diaper of claim 3, wherein the first and second adjustable stop mechanisms and the first and second bands are accessible via an opening in the diaper body.

5. The reusable diaper of claim 1, wherein the first casing and the second casing are formed at least in part by the first layer of the diaper body.

6. The reusable diaper of claim 1, wherein the first casing is coupled proximate to a first leg opening portion of the diaper body and the second casing is coupled proximate to a second leg opening portion of the diaper body.

7. The reusable diaper of claim 3, wherein the first channel narrows at the second end of the first channel to prevent the first adjustable stop mechanism from entering the first channel and the second channel narrows at the second end of the second channel to prevent the adjustable stop mechanism from entering the second channel.

8. A method of forming a reusable diaper, comprising:
forming a diaper body including an outer layer adapted to face away from a wearer and an inner layer adapted to face toward the wearer;
forming a first channel from a first casing that includes the inner layer and outer layer, wherein the first channel is between the inner layer and the outer layer of the first casing and is proximate to a first leg opening portion of the diaper body;
forming a second channel from a second casing that includes the inner layer and outer layer, wherein the second channel is between the inner layer and the outer layer of the second casing and is proximate to a second leg opening portion of the diaper body;
fixing a portion of a first band proximate to one or more of the diaper body and the first casing at a first end of the first channel;
placing the first band in the first channel and in a first adjustable stop mechanism that holds the first band in place at any number of locations on the first band at a second end of the first channel, wherein a length of the first band in the first channel is adjustable at the second end of the first channel via the first adjustment mechanism at a second end of the first channel and wherein a length of the first band outside of the first channel and the first adjustment mechanism are adapted to be positioned between the inner layer and the outer layer of the diaper body;
fixing a portion of a second band proximate to one or more of the diaper body and the second casing at a first end of the second channel; and
placing the second band in the second channel and in a second adjustable stop mechanism that holds the second band in place at any number of locations on the second band at a second end of the second channel, wherein a length of the second band in the second channel is adjustable at the second end of the second channel via the second adjustment mechanism at a second end of the second channel and wherein a length of the second band outside of the second channel and the second adjustment mechanism are adapted to be positioned between the inner layer and the outer layer of the diaper body.

9. The method of claim 8, wherein the method includes adjusting the first band at the second end of the first channel to fit a leg of the wearer.

10. The method of claim 8, wherein the method includes adjusting the second band at the second end of the second channel to fit a leg of the wearer.

11. The method of claim 8, wherein the method includes inserting an absorption layer between the inner layer and the outer layer.

12. The method of claim 8, wherein the method includes inserting an absorption layer adjacent to an outer surface of the inner layer wherein the absorption layer is positioned between the inner layer and the wearer.

13. The method of claim 8, wherein the method includes placing the diaper around the waist and legs of the wearer by coupling a first end of the diaper to a second end of the diaper.

14. A reusable diaper system, comprising:
a diaper body having an outer layer and an inner layer;
wherein the outer layer includes a fastening mechanism that couples a first end of the outer layer to a second end of the outer layer to form a first opening and a second opening for a wearer's leg to be placed through;
wherein a first channel is formed between the outer layer and the inner layer and is proximate to a first leg opening portion of the diaper, the first channel contains a first band, a second channel is formed between the outer layer and the inner layer and is proximate to a second leg opening portion of the diaper, and the second channel contains a second band;
wherein the first band is fixed to the diaper body at a first end of the first channel, the second band is fixed to the diaper body at a first end of the second channel, a length of the first band in the first channel is adjustable at a second end of the first channel via a first adjustable stop mechanism, and a length of the second band in the second channel is adjustable at a second end of the second channel via a second adjustable stop mechanism; and
wherein a length of the first band outside of the first channel and the first adjustment mechanism are adapted to be positioned between the inner layer and the outer layer of the diaper body and a length of the second band outside of the second channel and the second adjustment mechanism are adapted to be positioned between the inner layer and the outer layer of the diaper body.

15. The diaper system of claim 14, wherein an absorption layer is positioned between the outer layer and the inner layer.

16. The diaper system of claim 15, wherein the inner layer includes an opening to receive the absorption layer between the outer layer and the inner layer.

17. The diaper system of claim 14, wherein an absorption layer is adjacent to an outer surface of the inner layer and wherein the absorption layer is positioned between the inner layer and a wearer.

18. The diaper system of claim 14, wherein the fastening mechanism that couples the first end of the outer layer to the second end of the outer layer is selected from the group consisting of a button, a snap, a pin, and hook and loop fasteners.

19. The diaper system of claim 14, wherein the first adjustable stop mechanism is provided on the first band and the second adjustable stop mechanism is provided on the second band and wherein the first and second adjustable stop mechanisms and their respective channels are constructed and arranged to prevent the first and second adjustable stop mechanisms from entering the second end of their respective channel and the first and second adjustment stop mechanisms prevent the length of the first and second bands outside of each respective channel from entering their respective channel.

20. The diaper system of claim 14, wherein the first and second adjustable stop mechanisms are accessible via an opening in the diaper body.

* * * * *